US 8,524,207 B2

(12) United States Patent
Ellis et al.

(10) Patent No.: US 8,524,207 B2
(45) Date of Patent: Sep. 3, 2013

(54) COSMETIC COMPOSITIONS

(75) Inventors: Paul Ellis, Hull (GB); Tracey Heeson, Hull (GB); Mark Thomas, St. Peters, MO (US)

(73) Assignee: Reckitt Benckiser (UK) Limited, Slough, Berkshire, Slough (GB)

( * ) Notice: Subject to any disclaimer, the term of this patent is extended or adjusted under 35 U.S.C. 154(b) by 521 days.

(21) Appl. No.: 11/991,676

(22) PCT Filed: Sep. 18, 2006

(86) PCT No.: PCT/GB2006/003479
§ 371 (c)(1),
(2), (4) Date: Jan. 12, 2009

(87) PCT Pub. No.: WO2007/031793
PCT Pub. Date: Mar. 22, 2007

(65) Prior Publication Data
US 2009/0117068 A1 May 7, 2009

(30) Foreign Application Priority Data

Sep. 16, 2005 (GB) .................................. 0518934.5
Feb. 2, 2006 (GB) .................................. 0602109.1

(51) Int. Cl.
*A61K 8/30* (2006.01)
*A61K 8/36* (2006.01)
*A61Q 19/00* (2006.01)
*A61Q 5/00* (2006.01)
*A61Q 7/00* (2006.01)

(52) U.S. Cl.
USPC ..... 424/70.12; 424/73; 424/70.11; 424/70.13

(58) Field of Classification Search
None
See application file for complete search history.

(56) References Cited

U.S. PATENT DOCUMENTS

| 3,194,736 | A | | 7/1965 | Braun |
| 3,298,919 | A | | 1/1967 | Bishop, Jr. et al. |
| 4,074,429 | A | | 2/1978 | Roberts |
| 4,584,126 | A | | 4/1986 | Joshi |
| 4,874,392 | A | | 10/1989 | Henzi |
| 4,923,478 | A | * | 5/1990 | Naggiar ............................ 8/161 |
| 5,139,770 | A | | 8/1992 | Shih et al. |
| 5,174,992 | A | | 12/1992 | Lindauer et al. |
| 5,296,476 | A | | 3/1994 | Henderson |
| 5,482,644 | A | | 1/1996 | Nguyen et al. |
| 5,650,140 | A | * | 7/1997 | Bergmann et al. .............. 424/65 |
| 5,725,847 | A | | 3/1998 | De La Mettrie |
| 6,090,375 | A | | 7/2000 | Rechelbacher et al. |
| 6,484,737 | B1 | | 11/2002 | Muller et al. |
| 2002/0090386 | A1 | | 7/2002 | Haslwanter et al. |
| 2002/0198119 | A1 | * | 12/2002 | George ........................ 510/130 |
| 2003/0206878 | A1 | | 11/2003 | Gott et al. |
| 2004/0247545 | A1 | | 12/2004 | Jonas et al. |
| 2005/0123487 | A1 | | 6/2005 | Spadini |
| 2005/0129653 | A1 | * | 6/2005 | Hessefort et al. .......... 424/70.16 |
| 2005/0227887 | A1 | * | 10/2005 | Abbas .......................... 510/141 |

FOREIGN PATENT DOCUMENTS

| DE | 196 45 214 | | 12/1997 |
| EP | A 0 251 679 | | 6/1987 |
| EP | A 1 216 684 | | 6/2002 |
| GB | 1 255 284 | A | 12/1971 |
| GB | 2 009 017 | A | 6/1979 |
| WO | WO 96/32922 | | 10/1996 |
| WO | WO A 98/38965 | | 9/1998 |
| WO | WO A 02/15865 | | 2/2002 |
| WO | WO 03/009823 | A2 | 2/2003 |
| WO | WO 2004/082905 | A | 9/2004 |
| WO | WO 2004/089315 | A | 10/2004 |

OTHER PUBLICATIONS

Alander et al. In Cosmetics and Toiletries Manufacture Worldwide, 28, 30-32, 2002.*
DowAMS-C30CosmeticWax (www.russochemie.ru/files/dc/ams-c30.pdf), 2001.*
Girboux et al. In Happi Magazine, Dec. 1, 2005.*
Combined Search and Examination Report under Sections 17 and 18(3), GB0602109.1, dated Jun. 19, 2006.
Invitation to Pay Additional Fees which is attached to Partial International Search, PCT/GB2006/003479.
PCT International Preliminary Report on Patentability, PCT/GB2006/003479, dated May 6, 2008.
Van Reeth et al., "Alkylmethylsiloxanes as SPF enhancers. Relationship between effects and physic-chemical properties," Poster Presented at the 19th IFSCC Congress. Sydney. Oct. 22-25, 1996. 9 pages.
Van Reeth et al., "New silicone-based solutions for suncare." Dow Corning. 2003. 9 pages.
Starch et al., Expanding silicone technologies for sun care: performance complements aesthetics, 2007, 15 pages.

* cited by examiner

*Primary Examiner* — Dennis Heyer
(74) *Attorney, Agent, or Firm* — TraskBritt

(57) ABSTRACT

The present invention relates to a solid cosmetic composition which includes a soap and/or a non-soap surfactant, a hair modification active and/or skin enhancing agent, and at least one silicone and/or mineral oil.

19 Claims, 1 Drawing Sheet

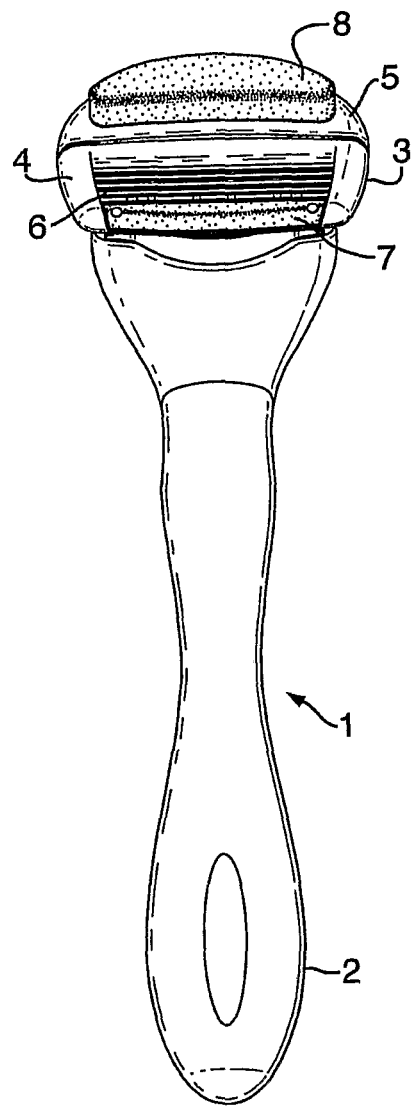

COSMETIC COMPOSITIONS

The present invention relates to a solid cosmetic depilatory composition and a shaving apparatus comprising the solid composition.

Various methods for removing hair from dermal surfaces are known. For example, hair may be removed from the skin using a depilatory composition. Such compositions typically take the form of creams or lotions and contain a depilatory active that is capable of degrading hair keratin.

In an alternative method, hair is removed from dermal surfaces using a razor. In a typical shaving method, the razor is moved across the surface of the skin; hair on the skin's surface is cut as it comes into contact with the razor blade(s). Optionally, a shaving aid, such as shaving cream, may be applied to the skin prior to shaving.

Although shaving provides an effective method of hair removal, the hair that is cut using a razor blade tends to have a hard and bristly appearance. It is therefore among the objects of the embodiments of the present invention to develop a composition that can be used to provide hair with an improved appearance, for example, after cutting.

According to a first aspect of the present invention, there is provided a substantially solid cosmetic composition including
a soap and/or a non-soap surfactant, and
a hair modification active.

The cosmetic composition is preferably a hair modification composition.

In this application, the term "solid" covers bodies that retain their shape without support at room temperature. The term does not cover flowable compositions, such as lotions, pastes and creams.

In this application the term hair modification covers both depilation (whereby the keratin present in hair is substantially broken down therefore effecting removal of the hair) and hair regrowth inhibition whereby an active is applied to a hair shaft or follicle thereby substantially reducing the hair regrowth. Hair modification is not intended to cover change the colour of hair by, for example, dying.

The hair modification active may be a depilatory active or an active which substantially inhibits the regrowth of hair (commonly known as a hair regrowth inhibitor or hair regrowth inhibition active).

The solid composition may be applied onto the skin like a conventional soap. For example, the solid composition may be applied onto the skin in the presence of water. Typically, at least a portion of the solid depilatory composition dissolves in water, for example, to form a lather.

The present invention further provides a method of modifying hair comprising:
applying the substantially solid cosmetic composition substantially as described hereinbefore onto the skin, optionally, in the presence of water;
permitting the composition to remain on the skin.

It is envisaged that when the hair modification composition is for use as a depilatory composition the composition remains on the skin for a residence time which is sufficient to degrade hairs on the skin.

The composition may be removed from the skin, together with depilated hair at the end of the residence time.

Preferably the residence time is less than 15 minutes, more preferably not more than 10 minutes, even more preferably not more than 8 minutes. Preferably the residence time is at least 1 second, more preferably at least 30 seconds, even more preferably at least 1 minute. Very suitably the residence time is to 2 to 6 minutes, about 3 to 5 minutes being especially preferred.

However, it is envisaged that when the composition is for use as a hair regrowth inhibitor the composition may remain on the skin indefinitely.

A further aspect of the invention provides a method of substantially reducing hair regrowth which method includes:
applying the solid composition substantially as described hereinbefore, to an area of skin to be treated, optionally in the presence of water,
leaving the composition on the skin for a residence time sufficient to substantially inhibit hair regrowth.

It is envisaged that the composition may be rinsed from the skin or allowed to remain on the skin indefinitely.

The composition may be removed from the skin by any means, for example using a sponge, spatula or scraper device.

The composition may also be removed by rinsing. However, it is also envisaged that the composition may remain on the skin indefinitely thereby not requiring rinsing. If rinsing or removal of the composition is not required it is particularly preferred that the pH of the composition is adjusted (such as to a pH in the range 4-8) so as to reduce irritation of the user.

Preferably, the composition includes at least one skin enhancing active. The skin enhancing active is preferably a compound which is typically used in skin care products. Such agents may reduce wrinkles, acne scarring, substantially reduce in-growing hairs, and/or chemically exfoliating the skin.

The at least one skin enhancing active is preferably a chemical exfoliating active such as an alpha hydroxyl acids (AHAs), such as salicylic acid, glycolic acid, lactic acid, malic acid, citric acid, tartaric acid, trichloracetic acid, or a Polyhydroxyacid (PHA), such as gluconalactone.

The chemical exfoliating active is typically present in an amount in the range 0.05 to 3.0% by weight of the composition, preferably 0.1 to 2.0% by weight of the composition, such as 0.5 to 1.5% by weight.

According to a further aspect of the present invention there is provided a substantially solid cosmetic composition including:
a soap and/or a non-soap surfactant, and
at least one skin enhancing active.

The cosmetic composition is preferably a skin enhancing composition.

The skin enhancing active is preferably a compound chemical exfoliating agent substantially as described hereinbefore.

It is particularly preferred that the composition includes a hair modification active. The hair modification active is substantially as described hereinbefore.

Accordingly, the present invention further extends to a method of enhancing mammalian skin, which method includes: applying a solid composition including a soap and/or non soap surfactant and a skin enhancing active, to the skin to be treated, optionally in the presence of water, leaving the composition on the skin for a predetermined time.

It is, of course, envisaged that the composition may be left in contact with the skin indefinitely.

As described above, the cosmetic compositions of the present invention may comprise soap. Preferably, soap is present in the solid hair modifying composition, optionally together with a non-soap surfactant. Suitable soaps are described in WO 96/32922 and WO 03/009823.

Suitable soaps include alkali metal (e.g. lithium, sodium or potassium), amine (e.g. alkanolamine) or ammonium salts of alkanoic or alkenoic acids having about 6 to 50 carbon atoms, preferably 8 to 22 carbon atoms, more preferably 12 to 20 carbon atoms. A mixture of two or more soaps may be employed.

The soap may be a salt of a fatty acid or a mixture of fatty acids. The fatty acid may be an animal or plant fatty acid. The fatty acid may be saturated, unsaturated and/or functionally substituted. The carbon chain length of the fatty acid may be selected to provide the soap with desired properties. Where a mixture of fatty acids is used, the carbon chain length of the fatty acids in the mixture may be selected to provide the soap with desired properties.

The soap may be made by any suitable method, for example, by direct saponification, optionally, in the presence of an alcohol. Natural fats and oils, such as tallow, fish oil, lard, grease, olive oil, palm oil, palm kernel oil, canola oil, castor oil (optionally, acetylated and/or hydrogenated), corn oil, cottonseed oil, peanut oil, safflower oil, soybean oil, sunflower oil, coconut oil, rice bran oil, neem oil, babassu oil, tall oil, sal oil, mowrah oil and/or karauja oil, may be saponified using procedures that are well known in the art. Mixtures of two or more oils may be used in the saponification reaction.

The soaps may be made by neutralising fatty acids (see above) with an alkali metal hydroxide or carbonate. Suitable hydroxides and carbonates include hydroxides and carbonates of lithium, sodium and potassium. Amines, such as alkanolamines may also be used in the neutralisation reaction. Examples include monoethanolamine, diethanolamine and triethanolamine. Fatty acids present in the fats and oils mentioned above may be used in the neutralisation reaction. Specific examples include lauric ($C_{12}$) acid, myristic ($C_{14}$) acid, palmitic ($C_{16}$) acid and/or stearic ($C_{18}$) acid. Palm fatty acids and palm kernel fatty acids may also be employed.

In one embodiment, the soaps may be made by neutralising a mixture of two or more fatty acids. The carbon chain length of each fatty acid in the mixture may be selected to provide the soap with particular characteristics. In one embodiment, a mixture of palm fatty acids and palm kernel fatty acids may be neutralised with an alkali metal hydroxide (e.g. sodium hydroxide). The mixture may include 60 to 90%, for example 80%, palm fatty acid and 10 to 30%, for example 20%, palm kernel fatty acid.

Examples of suitable soaps that may be used include sodium palmate, sodium palm kernelate, sodium laurate, sodium stearate (e.g. sodium iso-stearate) and sodium cocoate. Mixtures of such soaps may be employed.

In one embodiment, the soap comprises a sodium salt of distilled palm and lauric fatty acids. Specifically, the soap comprises a sodium salt of distilled 80% palm and 20% palm kernel fatty acids.

The soap may include other components conventionally present in soap compositions. Such components include unreacted fatty acid(s), chelating agents, such as tetra-sodium EDTA, and surfactants. Skin conditioning agents, such as glycerine (e.g. glycerine soaps), may also be present. Additives, such as crystallization retardants, may also be present.

Examples of suitable soaps include soaps sold under the PRISAVON™ trademark or the soap sold as PT Muslim S1000 soap noodles. The soap may be opaque or translucent.

As an alternative or in addition to the soap, a non-soap surfactant may be employed. Preferably, the non-soap surfactant is employed in addition to the soap. The non-soap surfactant may be a solid or a liquid. Suitable surfactants include cationic, anionic and/or non-ionic surfactants. Preferably, an anionic surfactant is employed. Suitable anionic surfactants include sodium cocoyl isethionate and sarcosinates, such as sodium lauryl sarcosinate. Mixtures of surfactants may be used. For example, in one embodiment, sodium cocoyl isethionate and sarcosinates are present in the solid depilatory composition. In an alternative embodiment, however, non-soap surfactants, such as sodium lauryl sulfate, are excluded from the composition.

The composition according to the present invention may comprise 40 to up to 99 weight %, preferably 45 to 98 weight %, more preferably 50 to 95 weight % soap and/or non-soap surfactant. It is, of course, envisaged that the composition may include more than one soap and/or non-soap surfactant.

In one aspect, the amount of soap and/or non-soap surfactant ranges from 80 to 93 weight %. In a preferred embodiment, the amount of soap and/or non-soap surfactant is from 85 to 91 weight %.

In a second aspect the composition includes at least one soap and at least one non-soap surfactant. Preferably, the combined weight of the soap and non-soap surfactant is 40 to 93 weight %, preferably 45 to 85 weight %, further preferably 55 to 75 weight %.

Where soap and non-soap surfactant(s) are present in the composition, the ratio of soap to non-soap surfactant(s) may be 100:1 to 1:100, preferably 20:1 to 1:20, more preferably 10:1 to 1:10, even more preferably 8:1 to 1:8, yet more preferably 4:1 to 1:4, for example 3:1 to 1:3. In one embodiment, the ratio of soap to non-soap surfactant is 2.5:1.

It is believed that many hair modification actives may have both depilatory and hair re-growth inhibition properties. It is further believed that the amount of hair modification active present and/or the pH in the hair modification composition determines whether the composition acts as a hair re-growth inhibition composition or a depilatory composition.

Accordingly, the composition when containing a hair modification active, may act as a depilatory composition or a hair re-growth inhibition composition. The hair modification active may therefore be selected from, but not restricted to a sulphur compound, such as potassium thioglycolate, sodium thioglycolate, ammonium thioglycolate, dithioetythritol, thioglycerol, thioglycol, thioxanthine, thipsalicylcic acid, N-acetyl-L-cysteine, lipic acid, $NaHSO_3$, $Li_2S$, $Na_2S$, $K_2S$, MgS, CaS, SrS, BaS, $(NH_4)_2S$, sodium dihydrolipoate 6,8-dithiooctanoate, sodium 6,8-dithiooctanoate, salts of hydrogen sulphide (e.g. NaSH or KSH), thioglycolic acid, thioglycerol, 2 mercaptopropionic acid, 3-mercaptropropionic acid, mercaptoethanol, dithioerythritol (DTE), gluatothione (reduced form), thiomalic acid, calcium thioglycolate, guanidine thioglycolate, glyceryl monothioglycolate, monoethanolamine thioglycolate, monoethanolamine thioglycolic acid, diammonium dithiodiglycolate, ammonium thiolactate, monoethanolamine thiolactate, thioglycolamide, homo-cysteine, cysteine, acetyl cysteine, glutathione, dithiothreitol, dihydrolipoic acid, 1,3-dithiopropanol, thioglycolamide, glycerolmonothioglycolate, thioglycolhydrazine, keratinase, hydrazine sulphate, hydrazine disulphate triisocyanate, guanidine thioglycolate, thiosalysilic acid, calcium thioglycolate, cysteamine, Xyleine, lipoic acid, sodium dihydrolipoate, thiolactic acid, thiopropionic acid, 2 thiolhistidene, 6 mercaptopurine, dimercaptosuccinic acid, thiophenol, 4-mthoxythiophenol, 4 bromothiophenol, benzyl mercaptan, 2 mercaptobenzothiazole, bromhexine, carbocysteine, domiodol, erdosteine, letosteine, lysozyme, mecysteine hydrochloride, mesna, sobrerol, stepronin, tiopronin, tyloxapol, nor-dihydroguaiaretic acid (NDGA), resveratrol and/or Bowman Birk inhibitor (BBI-AV). It is, of course, envisaged that blends of more than one hair modification active may be used.

Preferred hair modification actives are thioglycolates, or their precursor thioglycolic acid; glycerol monothioglycolate, cysteamine, acetyl cysteine (N-acetyl-L-Cysteine) and BBI-AV An example of a suitable thioglycolate is potassium thioglycolate, which may be produced by mixing thioglycolic acid with a neutralising source of potassium hydroxide.

The composition may comprise 0.01 to 30 weight %, preferably 0.05 to 20 weight %, more preferably 0.1 to 10 weight % of the hair modification active. In one embodiment, from 0.2 to 8 weight % depilatory active is present. In a preferred embodiment, the amount of depilatory active is 1 to 7 weight %, preferably 2 to 6 weight %.

It is particularly preferred that the composition includes at least one silicone and/or mineral oil.

The silicone is typically present in an amount greater than 5% by weight of the composition. Preferably, the silicone is present in an amount greater than 7% by weight of composition, further preferably greater than 10% by weight of the composition. It is particularly preferred that the silicone is present in an amount greater than 12.5% by weight of the composition, such as greater than 17.5% by weight of the composition.

The silicone is typically present in an amount no more than 75% by weight of the composition. Preferably, the silicone is present in an amount no more than 65% by weight of the composition, further preferably no more than 55% by weight of the composition, such as less than 45% by weight of the composition.

Accordingly, there is further provided a cosmetic composition comprising a soap and/or non-soap surfactant, and a silicone or mineral oil present in an amount greater than 5% by weight of the composition.

The silicone is typically present in an amount greater than 7.5% by weight of the composition. Preferably, the silicone is present in an amount greater than 10% by weight of composition, further preferably greater than 12.5% by weight of the composition. It is particularly preferred that the silicone is present in an amount greater than 15% by weight of the composition, such as greater than 17.5% by weight of the composition.

The cosmetic composition may be a hair modification composition which will include a hair modification active substantially as described hereinbefore. Alternatively, the composition may be a skin enhancing composition which includes a skin enhancing active substantially as described hereinbefore.

Cosmetic compositions containing soap and/or a non-soap surfactant together with silicone and/or mineral oil in an amount less than 5% by weight of the composition typically leave the skin feeling dry and/or dehydrated and are therefore not favoured by many users. Surprisingly, it has been found that by substantially increasing the amount of silicone present in a composition improves the feel of the composition on the skin. Furthermore, addition of higher levels of silicon and/or mineral oil increases the life time of the final composition as well as improving the hardness and durability of the composition. In addition, such cosmetic compositions are easier to transport as they are less prone to damage which affects both the aesthetic appeal of the cosmetic composition and possibly it's effectiveness.

The one or more silicone may be selected from C30-45 Alkyl Methicone and C30-45 Olefin, stearyl dimethicone, lauryl PEG/PPG-18/18 methicone, bis-hydroxyethoxypropyl dimethicone, poly dimethylsiloxane/vinyl co polymer, alkyl methyl siloxane wax, silicone glycol copolymer wax, cyclopenta siloxane, cyclo methicone, dimethicone, polydimethylsiloxone polymer, poly dimethyl siloxane, poly dimethicone, silicone glycol copolymer, a mixture of silicone elastomers in cyclopentasiloxane, trimethyl pentapheryl trisiloxane, sodium polyacrylate in dimethicone, polydimethylcyclosiloxane, polydimethiconol in cyclopentasiloxane, dimethiconsol, cyclo hexacyloxane, siloxane copolyol, polyphenylmethylsiloxane, trimethylsiloxy stearte and stearyl alcohol, silicone fluid, cyclomethicane (cyclopentacyloxane) dimethicane/vinyl dimethicane crosspolymer, polydimethyl siloxane (modified with a hydrocarbon).

Preferred silicones may include one or C30-45 Alkyl Methicone and C30-45 Olefin, stearyl dimethicane, lauryl PEG/PPG-18/18 methicone.

It is particularly preferred that the composition includes two or more silicone. Each silicone is selected for its properties which it imparts on the hair modification composition. For example, one or more silicone may provide body, hardness and structural integrity to the product. Alternatively, the one or more silicone may make the hair modification composition softer, improve the ease of spreading on the skin, reduces tackiness and/or provide a moisturising effect. Advantageously, when two or more silicone rubbers are included in the composition, each silicone rubber may provide a different physical property.

It is preferred that at least one silicone is present for its capability to provide structure and hardness to the composition. Preferably the composition includes C30-45 Alkyl Methicone and C3-45 olefin.

It is also preferred that at least one silicone is present for its ability to improve spreadability of the composition. Preferably the at least one silicone is selected from stearyl dimethicone and lauryl PEG/PPG 18/18 methicone.

According to a particularly preferred embodiment of the present invention, the hair modification composition includes C30-45 Alkyl Methicone and C30-45 Olefin, divinyldimethicone, Dimethicone copolymer and lauryl PEG/PPG-18/18 methicone.

Desirably, the C30-45 Alkyl Methicone and C30-45 Olefin is present in an amount in the range of 5% to 13% by weight of the composition, preferably 6% to 11% by weight of the composition, such as 7.5% to 9.5% by weight of the composition.

Desirably, the divinyldimethicone/dimethicone copolymer is present in an amount in the range of 3% to 9% by weight of the composition, preferably 4% to 8% by weight of the composition, such as 5% to 7% by weight of the composition.

Desirably, the Lauryl PEG/PPG-18/18 Methicone is present in an amount in the range of 3% to 9% by weight of the composition, such as 5% to 7% by weight of the composition.

The mineral oil is preferably selected from paraffin wax (such as cera microcristallina, hydrogenated microcristalline wax, paraffin, synthetic wax), paraffin oil (such as paraffinium liquidum), Carnauba wax (such as cera carnauba), Candelia wax, 030 Kerite, olive oil (such as ethyl olivate, hydrogenated olive oil, hydrogenated olive oil unsaponifiables, octyl dodecyl olivate, olivamide dea, olivamidopropyl dimethylamide, olive amidopropyl, dimethylamine lactate, olivamidopropylamine oxide, olive acid, olive oil PEG-6 esters, olive oil PEG-10 esters, PEG-4 olivate, potassium olivate, sodium olivate, sorbitan olivate, sulfated olive oil).

The solid composition of the present invention may additionally include a lathering agent, for example, to enhance or modify any lather produced when the composition is in use. Preferably the amount of the lathering agent is from 0.01 to 20 weight % relative to the weight of the composition. More preferably, the amount of lathering agent is from 0.1 to 10 weight %, for example, 0.5 to 5 weight %. In one embodiment, the lathering agent is present in an amount of 1 to 3 weight %. Suitable lathering agents include surfactants (e.g. dodecylbenzene sulfonate (DBS) and linear alkylaryl sulfonate (LAS)), glycerol, fatty acids and sugar. Preferably, glycerol is employed, for example, in an amount of 0.5 to 10 weight %, more preferably 0.5 to 1.5 weight % of the composition.

The solid composition of the present invention may additionally include a skin conditioning agent. The skin conditioning agent may act as a moisturiser and/or humectant. Suitable skin conditioning agents include allantoin, shea butter, cocoa butter, goa butter, kukui nut oil, coconut oil, castor oil, palm oil, olive oil, avocado oil, apricot kernel oil, sweet almond oil and hemp oil, aloe vera, glycerine, petrolatum, silk extracts, lavender extracts, wheatgerm oil and/or lotus milk or extract. Other skin conditioning agents include thick mineral oils (e.g. paraffin oil), isohexane and sunflower seed oil. Preferably, shea butter is employed.

The skin conditioning agent may be present in an amount of 0.01 to 20 weight %, preferably 0.05 to 10 weight %, more preferably 0.1 to 5 weight %, for example 0.5 to 2 weight % of the solid hair modification composition.

Optionally, the solid composition includes an accelerator that will accelerate the keratin degradation reaction such as urea, thiourea, dimethyl, isosorbide (DMI), ethoxydiglycol (Transcutol) or methyl propyl diol (MP diol). Preferably the accelerator is urea.

It is also envisaged that the composition may further include a UV stabilizer. Suitable UV stabilizers include sodium benzotriazolyl butylphenol sulphonate, or benzophenone-3.

The composition may also include one or more anti-oxidants. Suitable anti-oxidants include butylated hydroxytoluene, butylated hydroxyanisol, pentaerythrityl tetra-di-t-butyl hydroxyhydrocinnate or dimethylhexyl Syringylidene Malonate.

It is further envisaged that the composition may include a starch. A suitable starch would be, but not limited to maltodextrin/dextrin, although other starches suitable for use in cosmetic formulations may be used. The starch may be present in the range 0.1 to 45.0 by weight of the composition. It is envisaged that the amount of soap and/or non-soap surfactant may be reduced when a starch is present.

The solid composition may also include a fragrance. The fragrance may be present in an amount of 0.01 to 5 weight %, preferably 0.1 to 2 weight %, for example 0.7 weight %.

The solid composition may optionally include a dye or pigment, such as titanium dioxide. The dye or pigment may be present in an amount of 0.001 to 5 weight %, for example 0.001 to 1 weight % of the composition.

Optionally, a substance (e.g. a solvent) may be included in the solid composition to ensure that the components, such as the dye or pigment, of the composition are evenly distributed throughout the composition. For example, an alkylene glycol, such as propylene glycol, may be mixed with the dye or pigment (e.g. to form a paste) to ensure that the dye is evenly dispersed in the composition. The alkylene glycol (e.g. propylene glycol) may form from 0.001 to 5 weight %, preferably 0.01 to 3 weight % of the composition.

The solid composition may optionally include a vitamin, such as Vitamin E or Vitamin A. Vitamins may be present in an amount of from 0.01 to 10 weight % of the solid hair modification composition. Preferably, the one or more vitamins are present in an amount of 0.01 to 5 weight %, for example, 0.1 to 1 weight %.

The solid composition may optionally contain a binding agent. An example of a suitable binding agent is a clay, such as kaolin. Other examples include gums, resins, waxes (e.g. beeswax) and fatty alcohols. Binding agents may be used in a concentration of 0.001 to 5 weight %, preferably 0.01 to 5 weight % of the solid hair modification composition. Fillers, such as mica, talc, titanium dioxide and silica may also be included in the solid hair modification composition. Other fillers include dextrin, salt, borax, gypsum and starch. The amount of filler may range from 0.001 to 5 weight %, preferably 0.01 to 5 weight % of the solid hair modification composition.

The solid composition may include water, for example, in an amount of less than 50 weight %, preferably less than 30 weight %, more preferably less than 20 weight %, even more preferably less than 15 weight %, yet more preferably less than 10 weight % of the composition. In one embodiment, the solid depilatory composition comprises less than 5 weight % water.

Optionally, plasticizers and moulding aids may also be included in the solid composition.

In one embodiment, the composition soap, glycerol, shea butter and glycerolmonothioglycolate. Optionally, a fragrance, a dye and/or Vitamin E is included in the composition.

The solid composition of the present invention may be in the form of a soap bar. The soap bar may be moulded, for example, by extrusion moulding or compression moulding. The bar may be any suitable shape. For example, in one embodiment, the bar is shaped so that it can be housed in the shaving head of a shaving apparatus (razor).

The solid composition may be made, for example, by first mixing soap noodles until pliable. The remaining components of the composition may then be added to the soap mixture. Mixing is preferably continued until all components are evenly blended. Mixing may be carried out in more than one stages, for example, by passing the mixture through a mill more than once.

Once the components are evenly mixed, the mixture may be moulded, for example, by extrusion moulding. The moulding step may be carried out at a temperature of 20 to 80° C., preferably 30 to 50° C., for example 40° C.

The mixture may optionally be subjected to a reduced pressure or vacuum prior to the moulding step to reduce the risk of formation of air bubbles on the surface of the solid hair modification composition.

According to a further aspect of the present invention, there is provided a method of manufacturing a composition comprising a soap and/or a non-surfactant and at least one silicone and/or mineral oil, the method comprising:

a) heating a mixture of soap and/or non-soap surfactant to a temperature in the range of 75° C. to 85° C.;

b) blending the soap and/or non-soap surfactant with at least one silicone and/or mineral oil at a temperature in the range of 75° C. to 85° C.; and c) milling the blend obtained in b) so as to form soap ribbons.

Preferably the one or more silicones are pre-blended prior to step b).

The compositions of the present invention may be employed as a shaving aid. For example, the compositions of the present invention may be applied to the surface of the skin prior to or, preferably, after shaving. The composition may be wet with water before being contacted with the skin. Alternatively or additionally, the composition may be applied to wet skin. As mentioned above, at least a portion of the composition typically dissolves in water, optionally, to form a lather.

The composition may be housed in or adjacent the shaving head of a razor and at least partially released when the shaving head comes into contact with, for example, a moist dermal surface.

Accordingly, there is provided a shaving apparatus including a shaving head and having arranged thereon a substantially solid hair modification composition. The hair modification composition typically includes a soap and/or non-soap surfactant. The composition is preferably substantially as described hereinbefore.

According to yet further aspect of the present invention there is provided a shaving apparatus including a shaving head and the solid hair modification composition substantially as described above. At least a portion of the solid hair modification composition is desirably configured to directly contact the skin when the shaving apparatus is in use.

There is further provided a shaving apparatus including a shaving head and having arranged thereon a substantially solid skin enhancing composition. The skin enhancing composition typically includes a soap and/or non-soap surfactant. The composition is substantially as described hereinbefore.

According to still yet a further aspect of the present invention there is provided a shaving apparatus including a shaving head having arranged thereon a substantially solid composition, wherein the composition includes a soap and/or a non soap surfactant, and at least one silicone and/or mineral oil. At least a portion of the substantially solid composition is configured to directly contact the skin when the shaving apparatus is in use. Optionally the composition according to this aspect of the present invention includes a hair modification active and/or skin enhancing active substantially as described hereinbefore.

According to still yet a further aspect of the present invention there is provided a shaving apparatus including a shaving head having arranged thereon a substantially solid composition, wherein the composition includes a soap and/or a non soap surfactant, and at least one hair modification active. At least a portion of the substantially solid composition is configured to directly contact the skin when the shaving apparatus is in use.

According to still yet a further aspect of the present invention there is provided a shaving apparatus including a shaving head having arranged thereon a substantially solid composition, wherein the composition includes a soap and/or a non soap surfactant, and at least one skin enhancing active. At least a portion of the substantially solid composition is configured to directly contact the skin when the shaving apparatus is in use.

Alternatively or additionally, some of the solid composition may partially dissolve in water and the resulting solution containing dissolved composition may contact the skin. This solution may help to reduce drag effect which may occur between the shaving apparatus and the skin when the shaving apparatus is in use. It is, however, envisaged that the solid hair modification composition, prior to dissolution in water, may also help to reduce drag effect which may occur between a shaving apparatus and skin when the shaving apparatus is in use.

By applying the solid composition, when it contains a hair modification active onto the skin, the composition may act on the freshly cut hairs to provide the hairs with a more rounded and/or soft appearance. Providing the hairs with a more rounded and/or soft appearance is particularly advantageous as resultant hair re-growth may be substantially more aesthetically pleasing to the user of the shaver apparatus according to the present invention.

Alternatively, the composition may advantageously substantially degrade the hair or substantially reduce hair re-growth.

The shaving apparatus typically includes a handle which may be releasably connectible to the head. It is, however, envisaged that the handle may be permanently fixed to the head.

In a preferred embodiment, the shaving head includes one or more blades, wherein the composition is positioned adjacent the one or more blades. The composition may be present in or form a glide or lubrication strip, arranged as part of the shaving apparatus.

The shaving apparatus may be contacted with water before use, for example, to moisten the solid composition. Alternatively or additionally, the shaving apparatus may be used on pre-moistened skin. Once the shaving operation is complete, the skin may be rinsed with water.

Advantageously, the composition is positioned substantially adjacent one or more blades on the shaving head.

It is particularly preferred that the shaving head includes a blade pack housing arranged to house the at least one blade, and a soap box housing arranged to house the composition.

The composition may be in the form of a bar which is arranged on the blade pack housing. However it is also envisaged that the composition is housed in or on a soap box housing, wherein the soap box housing is substantially adjacent and linked to the blade pack housing. According to a particularly preferred embodiment the soap box housing is pivotally connected to or hinged to, the blade pack housing.

The following Examples further illustrate the present invention.

EXAMPLE 1

A hair modification composition was prepared from the following ingredients:

| Component | weight % |
| --- | --- |
| Soap Noodles (sodium Palmitate) | 54.1 |
| Sodium Stearate | 10.50 |
| Sodium Cocoyl Isethionate | 12.3 |
| C30-45 Alkyl Methicone and C30-45 Olefin | 9 |
| Divinyldimethicone/Dimethicone Copolymer and C12-13 Pareth D-23 and C12-13 Pareth B | 4.1 |
| Lauryl PEG/PPE - 18/18 Methicone | 4.1 |
| Cetearyl Alcohol | 2.4 |
| Guar hydroxypropyltrimonium Chloride | 1.1 |
| Shea Butter | 0.2 |
| Fragrance | 0.7 |
| N-Acetyl-L-Cysteine | 1.5 |

In this example, the soap noodles are refined through a plodder prior to mixing with the sodium stearate. Cetearyl alcohol is heated to at least 70° C. such that it becomes molten prior to blending with the sodium stearate. The silicones are heated to above 70° C. and blended with the previously blended silicones, soap noodles and sodium stearate. The remaining ingredients are subsequently added.

The resultant composition is milled at least 3 times into fine ribbons which are subsequently extended through a plodder into the required sized soap bars.

EXAMPLE 2

A hair modification composition was prepared from the following ingredients:

| Component | weight % |
|---|---|
| Soap Noodles (sodium Palmitate) | 56.25 |
| Sodium Stearate | 19.35 |
| C30-45 Alkyl Methicone and C30-45 Olefin | 9 |
| Divinyldimethicone/Dimethicone Copolymer and C12-13 Pareth D-23 and C12-13 Pareth B | 4.1 |
| Lauryl PEG/PPE - 18/18 Methicone | 9 |
| Thick mineral oil | 0.5 |
| Shea Butter | 0.1 |
| Fragrance | 0.7 |
| N-Acetyl-L-Cysteine | 1 |

In this example, the soap noodles are refined through a plodder prior to mixing with the sodium stearate. The silicones are heated to above 70° C. and blended with the previously blended silicones, soap noodles and sodium stearate. The remaining ingredients are subsequently added.

The resultant composition is milled at least 3 times into fine ribbons which are subsequently extended through a plodder into the required sized soap bars.

EXAMPLE 3

A soap formulation was prepared from the following ingredients.

| Component | Weight % |
|---|---|
| Soap Noodles (sodium Palmitate) | 49.66 |
| Sodium Stearate | 7.64 |
| Sodium cocoyl Isethionate | 19.1 |
| Wacker 8030 VP (silicone) INU name | 8.5 |
| Divinyldimethicone Dimethicone Copolymer and C12-C13 Pareth - 23 and C12-C13 Pareth 3 | 6 |
| Lauryl PEG/PPG - 18/18 Methicone | 6.1 |
| Cetyl Alcohol | 2 |
| Guar Hydroxypropyltrimonium Chloride | 1 |

In this example, the solid composition was manufactured according to the method outlined Example 2.

The soap bar is subsequently attached to a razor head (such as the one shown in FIG. 1).

EXAMPLE 4

A soap formulation was prepared from the following ingredients:

| Components | % W/W |
|---|---|
| Soap noodles (Sodium Palmate, Sodium Palm Kernelate, Water, Glycerine, Palm Acid, Palm Kernel Acid, Sodium Chloride, Tetra Sodium EDTA, Etidronic Acid | 41.765 |
| Sodium Stearate | 11.46 |
| Sodium Cocoyl Isethionate | 19.1 |
| C30-45 Alkyl Methicone and C30-45 Olefin | 8.5 |
| Divinyldimethicone Dimethicone Copolymer and C12-C13 Pareth-23 and C12-C13 pareth-3 | 6 |
| Lauryl PEG/PPG-18/18 Methicone | 6.1 |
| Cetyl Alcohol | 2 |
| Guar Hydroxypropyltrimonium Chloride | 1 |
| Paraffinum Liquidum | 1 |
| CI 77289 | 0.025 |
| Per Gratissima Oil | 0.1 |
| Parfum | 0.7 |
| Ethylenediaminetetraacetic acid | 0.07 |
| 1-Hydroxyethylidene-1,1-Diphosphonic Acid | 0.18 |
| N-Acetyl-L-Cysteine | 2 |

The soap was manufactured according to the method given in Example 2.

EXAMPLE 5

A soap formulation was prepared from the following ingredients:

| INCI Name | % W/W |
|---|---|
| Sodium Palmate, Sodium Palm Kernelate, Water, Glycerine, Palm Acid, Palm Kernel Acid, Sodium Chloride, Tetra Sodium EDTA, Etidronic Acid | 39.027 |
| Sodium Stearate | 11.46 |
| Sodium Cocoyl Isethionate | 19.1 |
| C30-45 Alkyl Methicone and C30-45 Olefin | 8.5 |
| Divinyldimethicone Dimethicone Copolymer and C12-C13 Pareth-23 and C12-C13 pareth-3 | 6 |
| Lauryl PEG/PPG-18/18 Methicone | 6.1 |
| Cetyl Alcohol | 2 |
| Guar Hydroxypropyltrimonium Chloride | 1 |
| Per Gratissima Oil | 0.1 |
| Titanium Dioxide | 0.2 |
| CI 73360 | 0.012 |
| CI 17200 | 0.001 |
| Parfum | 0.7 |

-continued

| INCI Name | % W/W |
|---|---|
| Ethylenediaminetetraacetic acid | 0.07 |
| 1-Hydroxethylidene-1,1-Diphosphonic Acid | 0.18 |
| Glycolic Acid | 5.55 |

The soap was manufactured according to the method given in example 2.

EXAMPLE 6

A soap formulation was prepared from the following ingredients:

| INCI Name | % W/W |
|---|---|
| Sodium Palmate, Sodium Palm Kernelate, Water, Glycerine, Palm Acid, Palm Kernel Acid, Sodium Chloride, Tetra Sodium EDTA, Etidronic Acid | 43.577 |
| Sodium Stearate | 11.46 |
| Sodium Cocoyl Isethionate | 19.1 |
| C30-45 Alkyl Methicone and C30-45 Olefin | 8.5 |
| Divinyldimethicone Dimethicone Copolymer and C12-C13 Pareth-23 and C12-C13 pareth-3 | 6 |
| Lauryl PEG/PPG-18/18 Methicone | 6.1 |
| Cetyl Alcohol | 2 |
| Guar Hydroxypropyltrimonium Chloride | 1 |
| Per Gratissima Oil | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxethylidene-1,1-Diphosphonic Acid | 0.18 |
| Salicylic Acid | 1 |

The soap was manufactured according to the method given in example 2.

EXAMPLE 7

A soap formulation was prepared from the following ingredients:

| INCI Name | Trade Name | % W/W |
|---|---|---|
| Sodium Palmate, Sodium Palm Kernelate, Water, Glycerine, Palm Acid, Palm Kernel Acid, Sodium Chloride, Tetra Sodium EDTA, Etidronic Acid | PT Musim S1000 Noodles | 41.577 |
| Sodium Stearate | Sodium Stearate | 11.46 |
| Sodium Cocoyl Isethionate | Sodium Cocoyl Isethionate | 19.1 |
| C30-45 Alkyl Methicone and C30-45 Olefin | AMS C-30 | 8.5 |
| Divinyldimethicone Dimethicone Copolymer and C12-C13 Pareth-23 and C12-C13 pareth-3 | HMW 2220 | 6 |
| Lauryl PEG/PPG-18/18 Methicone | DC 5200 | 6.1 |
| Cetyl Alcohol | Lanette 16 | 2 |
| Guar Hydroxypropyltrimonium Chloride | Guar | 1 |
| Per Gratissima Oil | Avocado Oil | 0.1 |
| Titanium Dioxide | Titanium Dioxide | 0.2 |
| CI 73360 | Puricolour VRE1 | 0.012 |
| CI 17200 | Puricolour ARE33 | 0.001 |
| Parfum | Fragrence ROD/619/00 | 0.7 |
| Ethylenediaminetetraacetic acid | EDTA | 0.07 |
| 1-Hydroxethylidene-1,1-Diphosphonic Acid | EDHP | 0.18 |
| N-Acetyl-L-Cysteine | NAC | 2 |
| Salicylic Acid | Salicylic Acid | 1 |

The soap was manufactured according to the method given in Example 2.

EXAMPLE 8

A soap formulation was prepared from the following ingredients:

| INCI Name | % W/W |
|---|---|
| Sodium Palmate, Sodium Palm Kernelate, Water, Glycerine, Palm Acid, Palm Kernel Acid, Sodium Chloride, Tetra Sodium EDTA, Etidronic Acid | 43.177 |
| Sodium Stearate | 11.46 |
| Sodium Cocoyl Isethionate | 19.1 |
| Paraffinum liquidum | 20 |
| Cetyl Alcohol | 2 |
| Guar Hydroxypropyltrimonium Chloride | 1 |
| Aloe Barbadensis | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxethylidene-1,1-Diphosphonic Acid | 0.18 |
| N-Acetyl-L-Cysteine | 2 |

The soap was manufactured according to the method given in Example 2.

EXAMPLE 9

A soap formulation was prepared from the following ingredients:

| INCI Name | % W/W |
|---|---|
| Sodium Palmate, Sodium Palm Kernelate, Water, Glycerine, Palm Acid, Palm | 43.177 |

-continued

| INCI Name | % W/W |
|---|---|
| Kernel Acid, Sodium Chloride, Tetra Sodium EDTA, Etidronic Acid | |
| Sodium Stearate | 11.46 |
| Sodium Cocoyl Isethionate | 19.1 |
| Olive Oil | 20 |
| Cetyl Alcohol | 2 |
| Guar Hydroxypropyltrimonium Chloride | 1 |
| *Aloe Barbadensis* | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxethylidene-1,1-Diphosphonic Acid | 0.18 |
| N-Acetyl-L-Cysteine | 2 |

The soap was manufactured according to the method given in Example 2.

EXAMPLE 10

A soap formulation was prepared from the following ingredients:

| INCI Name | % W/W |
|---|---|
| Sodium Palmate, Sodium Palm Kernelate, Water, Glycerine, Palm Acid, Palm Kernel Acid, Sodium Chloride, Tetra Sodium EDTA, Etidronic Acid | 40.677 |
| Sodium Stearate | 11.46 |
| Sodium Cocoyl Isethionate | 19.1 |
| Paraffinum liquidum | 18 |
| Cera Carnauba | 4.5 |
| Cetyl Alcohol | 2 |
| Guar Hydroxypropyltrimonium Chloride | 1 |
| *Aloe Barbadensis* | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxethylidene-1,1-Diphosphonic Acid | 0.18 |
| N-Acetyl-L-Cysteine | 2 |

The soap was manufactured according to the method given in Example 2.

EXAMPLE 11

A soap formulation was prepared from the following ingredients:

| INCI Name | % W/W |
|---|---|
| Sodium Palmate, Sodium Palm Kernelate, Water, Glycerine, Palm Acid, Palm Kernel Acid, Sodium Chloride, Tetra Sodium EDTA, Etidronic Acid | 40.177 |
| Sodium Stearate | 11.46 |
| Sodium Cocoyl Isethionate | 19.1 |
| Paraffinum liquidum | 18 |
| Paraffin wax | 5.0 |
| Cetyl Alcohol | 2 |
| Guar Hydroxypropyltrimonium Chloride | 1 |
| *Aloe Barbadensis* | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxethylidene-1,1-Diphosphonic Acid | 0.18 |
| N-Acetyl-L-Cysteine | 2 |

The soap was manufactured according to the method given in Example 2.

EXAMPLE 12

A soap formulation was prepared from the following ingredients:

| INCI Name | % W/W |
|---|---|
| PEG (Can use ranges between 400-4000) | 54.287 |
| Sodium Cocoyl Isethionate | 19.1 |
| C30-45 Alkyl Methicone and C30-45 Olefin | 8.5 |
| Divinyldimethicone Dimethicone Copolymer and C12-C13 Pareth-23 and C12-C13 pareth-3 | 6 |
| Lauryl PEG/PPG-18/18 Methicone | 6.1 |
| Cetyl Alcohol | 2 |
| Guar Hydroxypropyltrimonium Chloride | 1 |
| *Aloe Barbadensis* | 0.1 |
| Titanium Dioxide | 0.2 |
| CI 73360 | 0.012 |
| CI 17200 | 0.001 |
| Parfum | 0.7 |
| N-Acetyl-L-Cysteine | 2 |

The soap was manufactured according to the method given in Example 2.

EXAMPLE 13

A soap formulation was prepared from the following ingredients:

| INCI Name/Component | % W/W |
|---|---|
| Soap Noodles (Sodium Palmate, Sodium Palm Kernelate, Water, Glycerine, Palm Acid, Palm | 44.477 |

-continued

| INCI Name/Component | % W/W |
|---|---|
| Kernel Acid, Sodium Chloride, Tetra Sodium EDTA, Etidronic Acid) | |
| Sodium Stearate | 11.46 |
| Sodium Cocoyl Isethionate | 19.1 |
| C30-45 Alkyl Methicone and C30-45 Olefin | 8.5 |
| Divinyldimethicone Dimethicone Copolymer and C12-C13 pareth-23 and C12-C13 pareth-3 | 6 |
| Lauryl PEG/PPG-18/18 Methicone | 6.1 |
| Cetyl Alcohol | 2 |
| Guar Hydroxypropyltrimonium Chloride | 1 |
| Per Gratissima Oil | 0.1 |
| Titanium Dioxide | 0.2 |
| CI 73360 | 0.012 |
| CI 17200 | 0.001 |
| Parfum | 0.7 |
| Ethylenediaminetetraacetic acid | 0.07 |
| 1-Hydroxyethylidene-1,1-Diphosphonic Acid | 0.18 |
| (Resveratrol) | 0.1 |

The soap was manufactured according to the method given in Example 2.

EXAMPLE 14

A soap formulation was prepared from the following ingredients:

| INCI Name | Trade Name | % W/W |
|---|---|---|
| C30-45 Alkyl Methicone and C30-45 Olefin | AMS C-30 | 23.88 |
| Lauryl PEG/PPG-18/18 Methicone | DC 5200 | 12.295 |
| | White Beeswax | 3.975 |
| | Candelia Wax | 4 |
| | Carnauba Wax | 4.335 |
| | Microwax | 4 |
| | Cetiol LC | 6.665 |
| | IPM | 8 |
| | Mineral Oil | 5.125 |
| | Ozokerite | 2 |
| | Olive Oil | 9.335 |
| Cetyl Alcohol (or cetearyl alcohol) | Lanette 16 | 4.1 |
| | Ceteareth-20 | 1.64 |
| | PEG 60 Castor Oil | 2.46 |
| Aqua | Deionised Water | 8.19 |

The soap was manufactured according to the method given in Example 2.

EXAMPLE 15

A soap formulation was prepared from the following ingredients:

| INCI Name | Trade Name | % W/W |
|---|---|---|
| C30-45 Alkyl Methicone and C30-45 Olefin | AMS C-30 | 18.52 |
| Lauryl PEG/PPG-18/18 Methicone | DC 5200 | 10.505 |
| | White Beeswax | 2.6 |
| | Candelia Wax | 2.285 |
| | Carnauba Wax | 2.48 |
| | Microwax | 2.285 |
| | Cetiol LC | 3.815 |
| | IPM | 4.58 |
| | Mineral Oil | 12.035 |
| | Ozokerite | 1.145 |
| | Olive Oil | 14.42 |
| | Crill 6 | 3.395 |
| | Crillet 4 | 3.395 |
| Aqua | Deionised Water | 18.54 |

The soap was manufactured according to the method given in Example 2.

EXAMPLE 16

A soap formulation was prepared from the following ingredients:

| INCI Name | Trade Name | % W/W |
|---|---|---|
| Maltodextrin/dextrin | Starch Index | 41.187 |
| Sodium Cocoyl Isethionate | Sodium Cocoyl Isethionate | 20 |
| Cetyl Alcohol | Lanette 16 | 15 |
| C30-45 Alkyl Methicone and C30-45 Olefin | AMS C-30 | 8.5 |
| Divinyldimethicone Dimethicone Copolymer and C12-C13 Pareth-23 and C12-C13 pareth-3 | HMW 2220 | 6 |
| Lauryl PEG/PPG-18/18 Methicone | DC 5200 | 6.1 |
| Aloe Barbadensis | Aloe Vera Gel Extract | 0.1 |
| Titanium Dioxide | Titanium Dioxide | 0.2 |
| CI 73360 | Puricolour VRE1 | 0.012 |
| CI 17200 | Puricolour ARE33 | 0.001 |
| Parfum | Fragrence ROD/619/00 | 0.7 |
| Methylisothiazolinone, Idopropynlbutylcarbamate | Microcare MTI | 0.2 |
| N-Acetyl-L-Cysteine | NAC | 2 |

The soap was manufactured according to the method given in Example 2.

EXAMPLE 17

A soap formulation was prepared from the following ingredients:

| INCI Name | Trade Name | % W/W |
|---|---|---|
| Sodium Palmate, Sodium Palm Kernelate, Water, Glycerine, Palm Acid, Palm Kernel Acid, Sodium Chloride, Tetra Sodium EDTA, Etidronic Acid | PT Musim S1000 Noodles | 44.577 |
| Sodium Stearate | Sodium Stearate | 11.46 |
| Sodium Cocoyl Isethionate | Sodium Cocoyl Isethionate | 19.1 |

-continued

| INCI Name | Trade Name | % W/W |
|---|---|---|
| C30-45 Alkyl Methicone and C30-45 Olefin | AMS C-30 | 8.5 |
| Divinyldimethicone Dimethicone Copolymer and C12-C13 Pareth-23 and C12-C13 pareth-3 | HMW 2220 | 6 |
| Lauryl PEG/PPG-18/18 Methicone | DC 5200 | 6.1 |
| Cetyl Alcohol | Lanette 16 | 2 |
| Guar Hydroxypropyltrimonium Chloride | Guar | 1 |
| Per Gratissima Oil | Avocado Oil | 0.1 |
| Titanium Dioxide | Titanium Dioxide | 0.2 |
| CI 73360 | Puricolour VRE1 | 0.012 |
| CI 17200 | Puricolour ARE33 | 0.001 |
| Parfum | Fragrence ROD/619/00 | 0.7 |
| Ethylenediaminetetraacetic acid | EDTA | 0.07 |
| 1-Hydroxethylidene-1,1-Diphosphonic Acid | EDHP | 0.18 |

The soap was manufactured according to the method given in Example 2.

EXAMPLE 18

A soap formulation was prepared from the following ingredients:

| INCI Name | Trade Name | % W/W |
|---|---|---|
| Sodium Palmate, Sodium Palm Kernelate, Water, Glycerine, Palm Acid, Palm Kernel Acid, Sodium Chloride, Tetra Sodium EDTA, Etidronic Acid | PT Musim S1000 Noodles | 35.577 |
| Sodium Stearate | Sodium Stearate | 11.46 |
| Sodium Cocoyl Isethionate | Sodium Cocoyl Isethionate | 19.1 |
| C30-45 Alkyl Methicone and C30-45 Olefin | AMS C-30 | 8.5 |
| Divinyldimethicone Dimethicone Copolymer and C12-C13 Pareth-23 and C12-C13 pareth-3 | Wacker 8030 VP HMW 2220 | 6 |
| Lauryl PEG/PPG-18/18 Methicone | DC 5200 | 6.1 |
| Maltodextrin/Dextrin | Starch Index | 7 |
| Cetyl Alcohol | Lanette 16 | 2 |
| Guar Hydroxypropyltrimonium Chloride | Guar | 1 |
| *Aloe Barbadensis* | *Aloe Vera* Gel Extract | 0.1 |
| Butyrospermum parkii | Shea Butter | |
| Titanium Dioxide | Titanium Dioxide | 0.2 |
| CI 73360 | Puricolour VRE1 | 0.012 |
| CI 17200 | Puricolour ARE33 | 0.001 |
| CI 77289 | Unipure Green dye | |
| Parfum | Fragrence ROD/619/00 | 0.7 |
| Ethylenediaminetetraacetic acid | EDTA | 0.07 |
| 1-Hydroxethylidene-1,1-Diphosphonic Acid | EDHP | 0.18 |
| N-Acetyl-L-Cysteine | NAC | 2 |

The soap was manufactured according to the method given in Example 2.

FIG. 1 represents a razor according to one aspect of the present invention.

Referring to FIG. 1, there is provided a razor generally indicated by the numeral 1. The razor 1 comprises a handle portion 2 and a head 3 which may be removable from the handle 2. The head 3 includes a blade pack housing 4 and a soap block housing 5. The blade pack housing 4 is resiliently hinged to soap block housing 5. The blade pack housing 4 includes a blade pack 6 and a lubrication strip 7. The soap block 8 is mounted on soap block housing 5. The soap bar 5 is manufactured according to the present invention and may be manufactured (but not limited to) the formulations identified in the Examples.

In use, the user passes the head 3 over the hair to be cut (not shown) in such a direction that the soap 5 passes over the skin after the blade 4 has cut the hair. The bar 5 subsequently leaves a residue on the shaved skin.

The invention claimed is:

1. A solid cosmetic composition comprising:
   a surfactant in an amount of about 50% to less than about 95% by weight;
   a hair modification active in an amount of 0.05 to 15 weight %;
   wherein the hair modification active is selected from the group consisting of glycerol monothioglycolate, N-acetyl-L-Cysteine, cysteamine, potassium thioglycolate and a Bowmann-Birk Inhibitor;
   less than 5 weight % water;
   a skin enhancing agent; and
   a silicone present in an amount greater than 5% by weight of the solid composition, wherein the pH of the solid cosmetic composition is between 4 and 8.

2. A composition according to claim 1, wherein the skin enhancing active is selected from the group consisting of alpha hydroxyl acids (AHAs), salicylic acid, glycolic acid, lactic acid, malic acid, citric acid, tartaric acid, trichloracetic acid, a Polyhydroxyacid (PHA), and gluconalactone.

3. A composition according to claim 1, wherein the skin enhancing active is present in an amount of between 0.1 and 2.0% by weight of the composition.

4. A composition according to claim 1, wherein the skin conditioning agent is present in an amount of between 0.01 and 10% by weight of the composition.

5. A composition according to claim 1, wherein the skin conditioning agent is shea butter.

6. A composition according to claim 1, wherein the silicone is present in an amount less than 75% by weight of the composition.

7. A composition according to claim 1, wherein the silicone is selected from the group consisting of C30-45 Alkyl Methicone and C30-45 Olefin, divinyldimethicone/Dimethicone copolymer and C12-13 Pareth-23 and C12-13 Pareth, stearyl dimethicone, Lauryl PET/PPG-18/18 Methicone, divinyldimethicone/dimethicone copolymer in emulsion form, declopentasiloxane, B15-PEG, and methyl ether dimethyl silane.

8. A composition according to claim 1, further comprising a starch.

9. The solid cosmetic composition of claim 1, wherein the composition is a solid soap bar that retains its shape without support at room temperature, and wherein the solid soap bar is capable of repeated use.

10. The solid cosmetic composition of claim 1, wherein the silicone is present in an amount of at least 7% by weight of the solid composition.

11. The solid cosmetic composition of claim 1, wherein the silicone is present in an amount in the range of 6% to 11% by weight of the solid composition.

12. A solid soap bar capable of repeated use, the solid soap bar comprising:
   surfactant in an amount of about 40% to less than about 95% by weight of the solid soap bar;
   a hair modification active; wherein the hair modification active is selected from the group consisting of glycerol monothioglycolate, N-acetyl-L-Cysteine, cysteamine, potassium thioglycolate and a Bowmann-Birk Inhibitor; and
   a silicone present in an amount greater than 5% by weight of the solid soap bar to increase the hardness and durability of the solid soap bar in comparison to a composition comprising the silicone present in an amount of 5% or less by weight, wherein the silicone is selected from the group consisting of C30-45 Alkyl Methicone and C30-45 Olefin, divinyldimethicone/Dimethicone copolymer and C12-13 Pareth-23 and C12-13 Pareth, stearoyl dimethicone, Lauryl PET/PPG-18/18 Methicone, divinyldimethicone/dimethicone copolymer in emulsion form, declopentasiloxane, B 15-PEG, and methyl ether dimethyl silane, so that the solid soap bar is capable of repeated use, wherein the pH of the solid soap bar is between 4 and 8.

13. The solid soap bar of claim 12, wherein the silicone is present in an amount of at least 7% by weight of the soap bar.

14. The solid cosmetic composition of claim 9, wherein the silicone is present in an amount of at least 7% by weight of the solid composition.

15. The solid soap bar of claim 12, wherein the silicone is present in an amount in the range of 6% to 11% by weight of the soap bar.

16. The solid cosmetic composition of claim 9, wherein the silicone is present in an amount in the range of 6% to 11% by weight of the solid composition.

17. A method of modifying hair including:
   applying the solid composition of claim 1 onto an area of skin to be treated, and
   leaving the composition on the skin for a residence time sufficient to modify the growth of hairs on the skin or to degrade at least some of the keratin in the hair on the skin.

18. A method according to claim 17, wherein the composition is removed from the skin after a predetermined period of time.

19. The method according to claim 18 wherein the solid composition is applied in the presence of water.

* * * * *